United States Patent [19]

Muchmore et al.

[11] Patent Number: 4,977,244

[45] Date of Patent: Dec. 11, 1990

[54] UROMODULIN AND A PROCESS OF PURIFYING IT

[75] Inventors: Andrew V. Muchmore, Potomac; Jean M. Decker, Rockville, both of Md.

[73] Assignee: The United States of America as represented by the Department of Health and Human Services, Washington, D.C.

[21] Appl. No.: 943,406

[22] Filed: Dec. 19, 1986

Related U.S. Application Data

[63] Continuation-in-part of Ser. No. 749,442, Jun. 27, 1985, abandoned.

[51] Int. Cl.$^5$ .......................... C07K 15/06; C07K 3/28
[52] U.S. Cl. ..................................... 530/350; 530/351; 530/395; 530/412; 530/413; 530/417; 530/834; 514/2; 514/8; 514/12; 514/21; 514/886; 514/885; 424/85.1; 424/85.2

[58] Field of Search ............... 530/350, 351, 395, 834, 530/412–413, 417; 424/85.1, 85.2; 514/2, 8, 21, 12, 886, 885

[56] References Cited

U.S. PATENT DOCUMENTS 4,661,447 4/1987 Fabricius et al. .................... 530/351
4,681,844 7/1987 Fabricius et al. .................... 530/351

OTHER PUBLICATIONS

Walsh, CA vol. 107, 1987, #37792p.
Roberts et al., J. Exp. Med. 163, 1986, pp. 511–119.

Primary Examiner—Garnette D. Draper
Attorney, Agent, or Firm—Robert Benson

[57] ABSTRACT

This invention relates to processes for producing uromodulin, a glycoprotein having a molecular weight of 85 kilo daltons. This glycoprotein, which is isolated from crude urine, as well as its carbohydrate derivatives, are useful as immunosuppressive agents or anti-inflammatory agents.

6 Claims, 14 Drawing Sheets

| SOURCE | VOLUME | TOTAL PROTEIN | UROMODULIN | YIELD |
|---|---|---|---|---|
| CRUDE PREGNANCY URINE | 6ml. | 720,000μg | 7080μg | 100% |
| ELUATE CON A COLUMN | 42ml. | 92,400μg | 5950μg | 84% |
| PEAK I FRACTOGEL | 6ml. | 2,800μg | 1810μg | 26% |
| ELUTED IEF GEL | 1.2ml. | 300μg | 300μg | 4% |

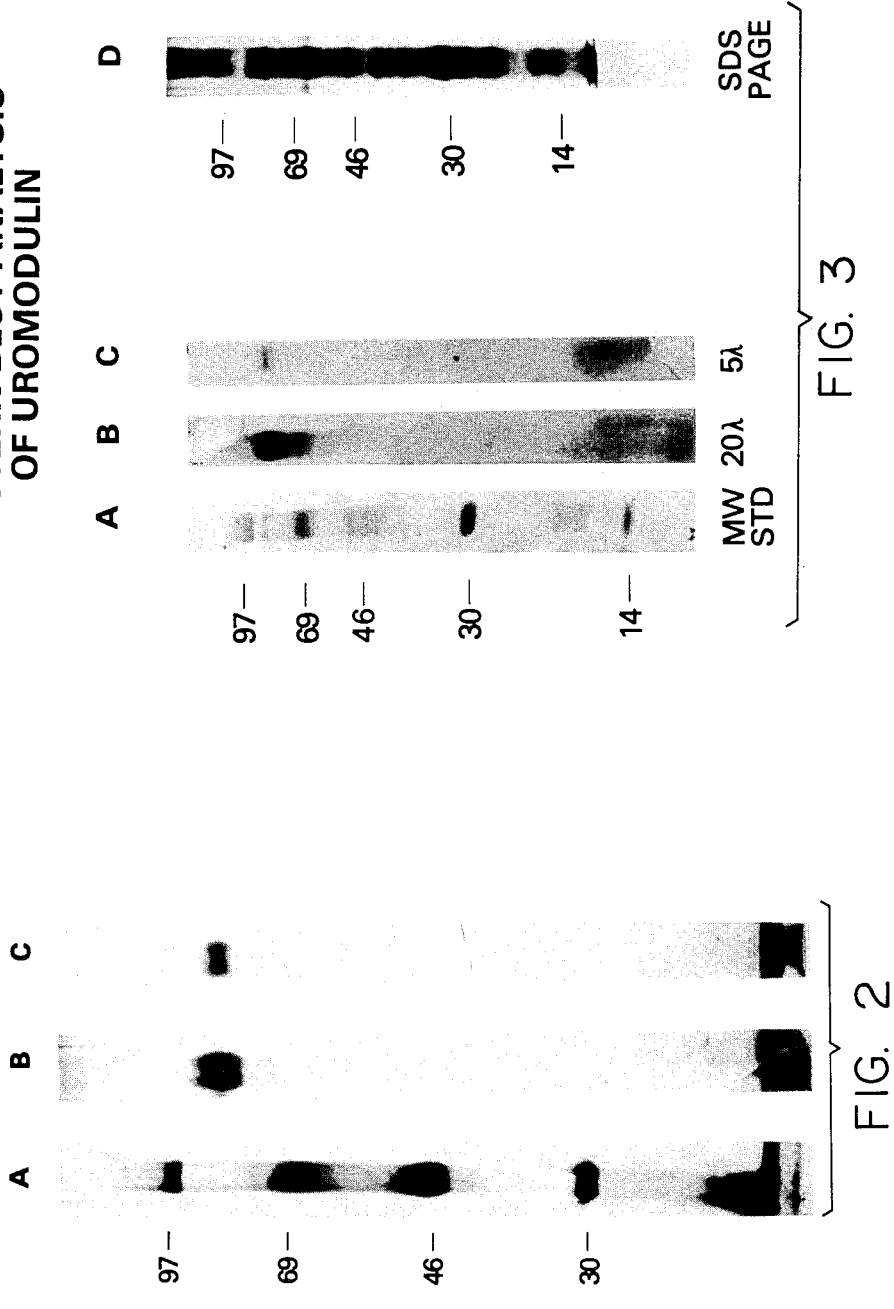

SDS-PAGE OF REDUCED AND UNREDUCED UROMODULIN

REDUCED UNREDUCED

N-GLYCANASE DIGESTED UROMODULIN IS IMMUNO SUPPRESSIVE

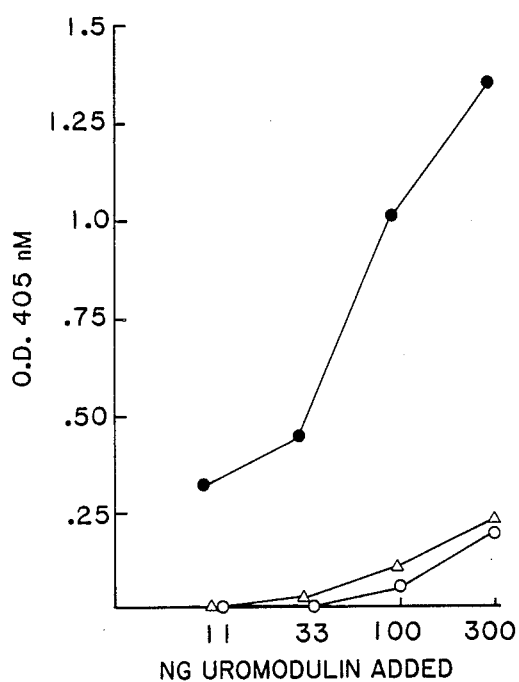

4,977,244

UROMODULIN AND A PROCESS OF PURIFYING IT

This application is a continuation-in-part of Ser. No. 06/749,442, filed June 27, 1985, now abandoned.

TECHNICAL FIELD OF INVENTION

This invention relates to processes for producing uromodulin, a glycoprotein having a molecular weight of 85 kilo daltons. More particularly, this invention relates to the isolation and characterization of uromodulin from crude urine and the purification of uromodulin to homogeneity as assessed by reduced or unreduced sodium dodecyl sulfate-polyacrylamide gel (SDS-PAGE). Uromodulin itself, or the carbohydrate portion thereof, is useful as an immunosuppressive agent and an anti-inflammatory agent.

BACKGROUND ART

During pregnancy, the histoincompatible placental unit is protected from maternal immuno-surveillance for reasons which to date remain unexplained (G. Chaout, "The Riddle of the Foetal Allograft", *Ann. Immunol.* (*Inst. Pasteur*, 135D, p. 301 (1984)). Various compounds associated with pregnancy have been proposed as the immunosuppressive agent responsible for this protection. These compounds include human chorionic gonadotropin, alpha fetoprotein, human placental lactogen, pregnancy associated plasma protein A and SP-1. Upon further analysis, however, none of these compounds has been identified as a useful immunoregulatory agent (A. V. Muchmore and R. M. Blaese, "Immunoregulatory Properties of Fractions From Human Pregnancy Urine: Evidence that Human Chorionic Gonadotropin Is Not Responsible", *J. Immunol.*, 118, p. 881 (1977); S. F. Contractor and H. Davies, "Effect of Human Chorionic Somatomammatropin and Human Chorionic Gonadotropin on Phytohemagglutinin Induced Lymphocyte Transformation", *Nature* (*New Biol.*), 243, p. 284 (1973); S. Yachin, "The Immunosuppressive Properties of Alpha Fetoprotein: A Brief Overview", *Ann. NY Acad Sci.*, 417, p. 105 (1983); W. H. Stimson, "Are Pregnancy - Associated Serum Proteins Responsible for the Inhibition of Lymphocyte Transformation by Pregnancy Serum?", *Clin. Exp. Immunology*, 40, p. 157–60 (1980); C. Cerni et al.,"Immunosuppression By Human Placental Lactogen and the Pregnancy Specific Beta-1 Glycoprotein (SP-1)", *Arch. Gynakol*, 223, p. 1 (1977); J. A. McIntyre et al., "Immunological Studies of the Human Placenta: Functional and Morphologic Analysis of PAPP-A", *Immunology*, 44, p. 577 (1981)).

To date therefore, although the importance in other immunosuppressive applications and therapy of the compounds responsible for the immunologic protection of the placenta from maternal immunosurveillance has been recognized, no such compounds have been isolated, purified or characterized.

DISCLOSURE OF THE INVENTION

This invention solves the problems referred to above by providing processes for producing and purifying to homogeneity uromodulin, a glycoprotein which has immunosuppressive and anti-inflammatory activity. Uromodulin is an 85 kilo dalton glycoprotein having about a 30% carbohydrate content. The carbohydrate portion of uromodulin is also characterized by immunosuppressive and anti-inflammatory activity.

BRIEF DESCRIPTION OF THE DRAWINGS

FIG. 2 depicts several SDS-PAGE analyses of fractions of uromodulin obtained at various fractionation steps of the process of this invention. Lane A depicts standard molecular weight markers. Lane B depicts uromodulin after concentration of peak 1 from FIG. 1B. Lane C depicts final purification of uromodulin after elution from an isoelectric focusing gel.

FIG. 3 depicts a Western Blot analysis of Con-A fractionated pregnancy urine. Lane A depicts molecular size standards stained with Amido Black. Lanes B and C depict the reactivity of rabbit serum used as a probe against a crude fraction of pregnancy urine. Lane D depicts the protein silver stain of 1 µl of the crude pregnancy urine fraction.

FIG. 13 depicts the inhibition by N-glycanase digestion of the ability of uromodulin to bind to interleukin-1.

DETAILED DESCRIPTION OF THE INVENTION

Figures 1A, 1B:
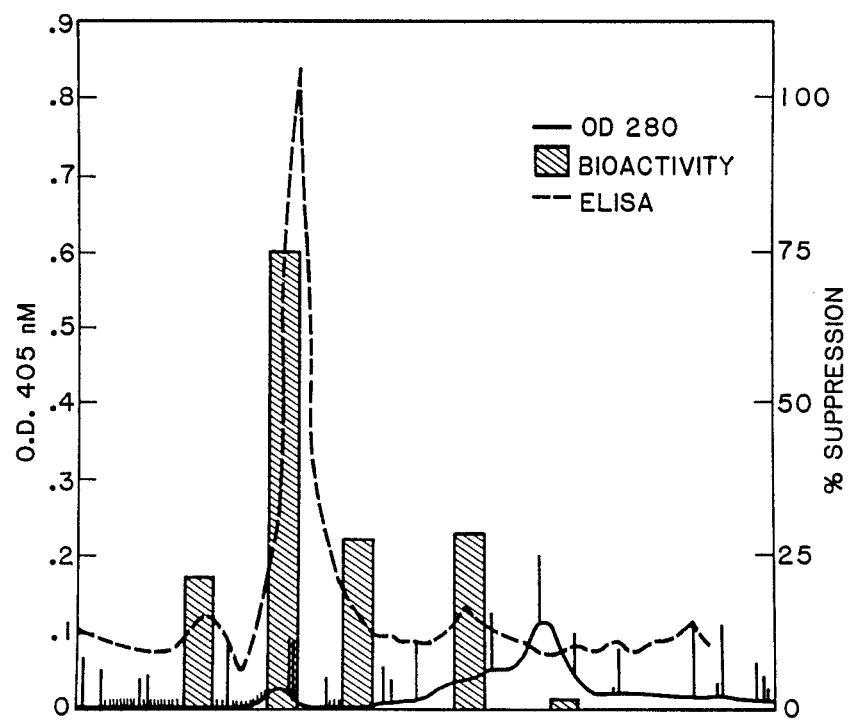
FIG. 1A depicts in tabular form the purification of uromodulin.
FIG. 1B depicts the elution pattern, bioactivity and immunoreactive profiles of uromodulin purified according to one embodiment to this invention.

This invention relates to processes for isolating and purifying uromodulin from crude human urine. According to this invention, uromodulin may be purified to homogeneity as assessed by sodium dodecyl sulfate-polyacrylamide gel electrophoresis (SDS-PAGE).

Generally, one embodiment of this process comprises the steps of contacting crude urine with an affinity column containing a lectin which recognizes mannose, eluting uromodulin from the column and dialyzing small molecular weight contaminants, i.e. contaminants having a molecular weight below about 10 kilo daltons, from the uromodulin. According to another embodiment, the process of this invention further comprises an isoelectric focusing purification step.

Uromodulin may be isolated from any human urine, as well as from pregnancy urine. In addition, it may be isolated from non-human pregnancy or non-pregnancy urine.

This invention also relates to the uromodulin produced according to the above-described processes. Uromodulin is an 85 kilo dalton glycoprotein having about a 30% carbohydrate content. It is a single peptide having intra-chain disulfide linkages. We believe that the active portion of uromodulin comprises the N-linked sugars.

Uromodulin is characterized by immunological and immuno-suppressant activities. For example, uromodulin suppresses antigen-specific T cell proliferation in vitro at concentrations as low as 100 pM. It also is a potent inhibitor of spontaneous monocyte cytotoxicity, acting at concentrations as low as $10^{-11}$M. In addition, uromodulin specifically binds and inhibits interleukin-1 (IL-1) and tumor necrosis factor (TNF). IL-1 and TNF are known to be mediators of immunoresponses such as inflammation. Accordingly, uromodulin's activity of binding and inhibiting IL-1 and TNF indicates its utility as an immunosuppressant or anti-inflammatory agent. Without being bound by theory, we believe that these activities are attributable to the N-linked glycosylation of the uromodulin molecule. Uromodulin is, therefore, advantageously useful in immunotherapeutic methods and compositions for treating mammals, including humans. Uromodulin itself, as well as the carbohydrate portions derived therefrom, are particularly useful as immunosuppressive or anti-inflammatory agents.

Uromodulin or uromodulin derivatives prepared according to the processes of this invention may be employed in a conventional manner in immunotherapeutic and anti-inflammatory methods and compositions. Such methods of treatment and their dosage levels and requirements are well-recognized in the art and may be chosen by those of skill in the art from available methods and techniques. For example, uromodulin or its carbohydrate derivatives may be combined with a pharmaceutically acceptable adjuvant for administration to a patient in an amount effective to provide immunosuppressant or anti-inflammatory effects and accordingly to lessen the severity of the target disease or symptoms. The dosage and treatment regimens will depend upon factors such as the patient's health status, the severity and course of symptoms and the judgment of the treating physician.

In order that the invention herein described may be more fully understood, the following examples are set forth. It should be understood that these examples are for illustrative purposes only and are not be construed as limiting this invention in any manner.

EXAMPLES

A. Preparation Of Uromodulin

According to one embodiment of this invention, we purified uromodulin from crude human pregnancy urine as follows. We collected and stored at $-20°$ C. unfractionated crude human urine from individual donors at 20-40 weeks of gestation. We passed six liters of urine over a lectin affinity column, preferably a concanavalin-A Sepharose column, (Pharmacia, Uppsala, Sweden) with a total bed volume of 200 ml. Although the use of Con A is preferred as described above, other lectins which recognize mannose, such as lentil lectin, may also be employed. We then washed the column with four bed volumes of phosphate-buffered saline (PBS). This resulted in the removal of 90% of the starting protein, while retaining 80-100% of the uromodulin. See FIG. 1a.

We then eluted the uromodulin from the column with two bed volumes of 250 mM methyl mannopyranoside in PBS and dialyzed the small molecular weight contaminants from the uromodulin for 48 hours at 4° C. against three changes of fifty volumes of distilled water. Although we used methyl mannopyranoside to elude the column, any mannose, pyranoside or saccharide which competes with the lectin in the affinity column may also be used. We then lyophilized and resuspended the dialysate in 15 ml PBS. As an alternative to these lyophilization and resuspension steps, other conventional procedures may be used to concentrate the uromodulin to an appropriate volume to be placed on a molecular sizing column. We separated the resuspended material on a molecular sizing column with a large exclusion pore size, preferably a 2.5×90 cm Fractogel 55S (Merck, Rahway, N.J., U.S.A.; exclusion limit 500 to 750 kilo daltons) by eluting the column with PBS. This resulted in resolution of uromodulin from the small molecular weight contaminants. At this stage, the only consistent contaminant on SDS-PAGE was a 30 kD material that co-purified with the uromodulin. The uromodulin obtained after this step was substantially homogeneous on 12.5% SDS-PAGE. Uromodulin migrated as the first peak, resulting in a 95% pure yield. See FIG. 1B and FIG. 2, Lane 2.

According to an alternate embodiment of this invention, the uromodulin obtained by the above-described process may be further purified by isoelectric focusing to resolve the 30 kD contaminant. For example, we pooled and dialyzed the first peak resolved above against distilled water, then resuspended the dialysate in 0.01M phosphate buffer at pH 7.0. We then loaded the resuspended dialysate onto preabsorbent wicks and focused the loaded wicks on precast isoelectric focusing (IEF) gels, pH 4.5 to 9.0 (LKB, Broma, Sweden). We collected the area directly under the wick and eluted it with distilled water. We then concentrated the eluate in filters, preferably Centricon filters (Amicon, Danvers, Mass., U.S.A.) with a cut-off of 30 kilo daltons. A molecular sieving high-performance liquid chromatography (HPLC) column, preferably TCK 3000 (Bio-Rad, Richmond, Calif., U.S.A.), was used when necessary, to remove any remaining focusing buffers.

Since uromodulin fails to aggregate in isoelectric gels, while contaminants migrate freely, the above-described process yielded a broad single 85 kilo dalton band on unreduced 12.5% SDS-PAGE. See FIG. 2, Lane C. Under reducing conditions with dithiothreitol, SDS-PAGE of uromodulin yielded a single band at 95 kilo daltons, suggesting that uromodulin is a single peptide with intra-chain disulfide linkages.

B. Assays Of Purified Uromodulin

At each fractionation step described above, we assayed the biological activity of the purified material by measuring the inhibition of tetanus toxoid induced T cell proliferation of normal human peripheral blood mononuclear cells using a modification of the assay described in A. V. Muchmore J. M. Decker and R. M. Blaese, "Evidence That Specific Oligosaccharides Block Early Events Necessary for the Expression of Antigen-Specific Proliferation by Human Lymphocytes", *J. Immunol.*, 125, pp. 1306-11 (1980).

In this assay, we centrifuged heparinized human blood at 200XG for 5 minutes in a RT 6000 (Sorvall) and collected the buffy coat layer of cells. We allowed the cells to settle in PBS for 30 minutes to remove clusters of platelets and then washed the cells two more times in PBS. We resuspended the cells in RPMI 1640, with added penicillin, streptomycin and glutamine. Subsequently, we incubated $2 \times 10^5$ viable cells in 10% autologous plasma with optimized concentrations of tetanus toxoid (Massachusetts Department Of Public Health) and added various concentrations of uromodulin or derivatives of uromodulin to a final volume of 0.2 ml. The cultures were then pulsed with 0.5 microcurie of $^3H$ thymidine for six hours on the sixth day and counted for $^3H$ thymidine incorporation.

Using this assay, we determined that purified uromodulin blocks in vitro antigen specific T cell proliferation to recall tetanus toxoid antigens at concentrations as low as 100 pM.

We also used our purified uromodulin as an immunogen to raise a heteroantibodies in rabbits. Subsequently, we used this antiserum as a probe in Western blot analysis of crude pregnancy urine.

The crude fractions of pregnancy urine were separated on 12.5% SDS-PAGE and transferred to nitrocellulose (Schleicher and Schuell protocols, S and S, Keene, N.H., U.S.A.). Bound antibody on the nitrocellulose was detected using a biotinylated goat antiserum to rabbit IgG, followed by an avidin-biotin-horseradish-peroxidase complex reagent (Vector, Burlingname, Calif., U.S.A.). This antibody fails to bind significantly to any protein found in normal human serum having a molecular weight of less than 150 kilo daltons. It did bind weakly in an area consistent with human IgG, which could not be removed by absorption of our antisera with immobilized human serum. This suggested that human antibody was recognizing the rabbit IgG. See FIG. 3.

FIG. 3, Lanes B and C depict the reactivity of the rabbit antiserum. Lane A represents molecular size standards stained with Amido black. Land D represents protein silver stain of 1 $\mu$l of the crude urine fraction. The analysis exhibited a single major band at 85 kilo daltons, with two minor bands seen only on overloaded gels.

As further evidence that the rabbit antiserum was recognizing an immunosuppressive molecule, we conjugated the antiserum to cyanogen bromide-activated Sepharose (Pharmacia, Uppsala, Sweden) and used it as a solid-phase immunoabsorbent. We adsorbed crude human pregnancy urine to this column, then washed it extensively and eluted it with 0.1M glycine buffer (pH =2.8). The eluate had a molecular weight of 85 kilo daltons on SDS-PAGE and exhibited immunosuppressive activity in vitro to tetanus toxoid (infra, page 10-11).

We also conjugated a purified immunoglobulin G (IgG) fraction of this antiserum to alkaline phosphatase and developed a sensitive direct quantitative enzyme-linked immunosorbent assay (ELISA) for uromodulin. The assay consisted of a sandwich assay such as that described by A. Voller et al. in *Manual Of Clinical Immunology*, pp. 359-71 (1980). See FIG. 1a.

Figure 4B:
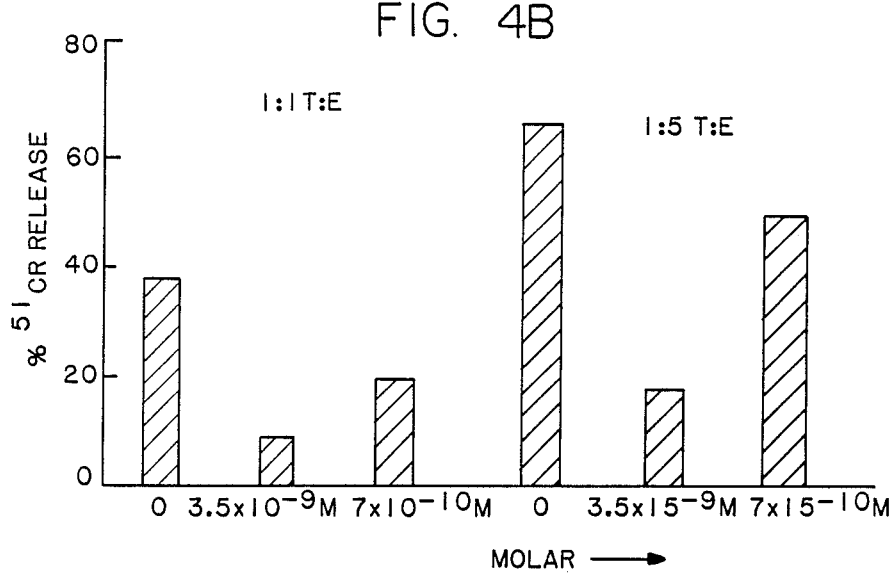
FIG. 4a depicts the dose-response function of uromodulin from a single donor added at the initiation of culture to human peripheral blood mononuclear cells stimulated with tetanus toxoid and subsequently harvested. 4B depicts the effect of uromodulin on the generation of spontaneous monocyte-mediated cytotoxicity.
Figure 4A:
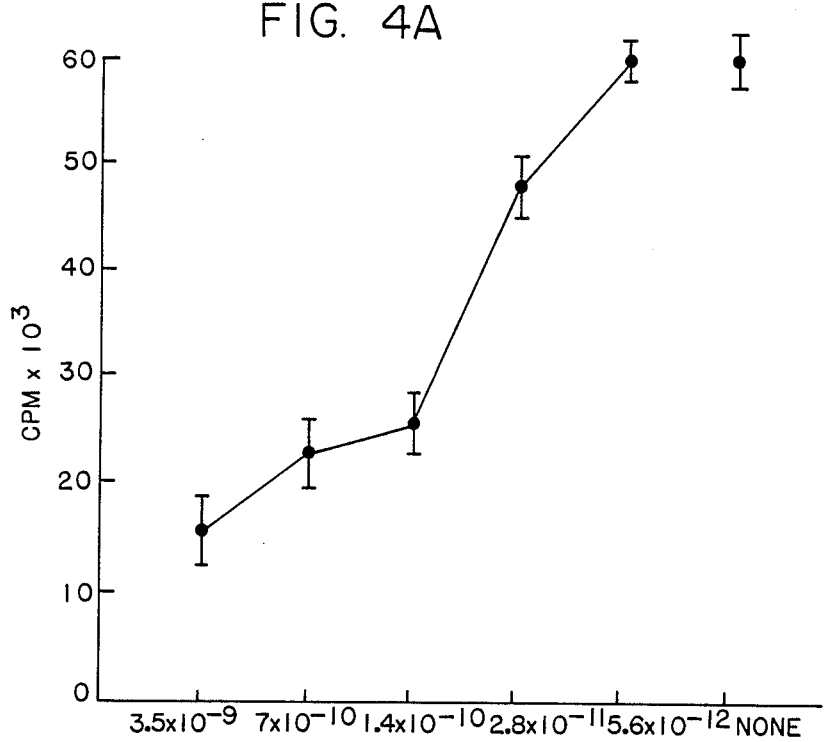

We then examined the in vitro bioactivity of the purified uromodulin obtained by the process set forth above. We measured the dose-response function of uromodulin added at the initiation of culture to human peripheral blood mononuclear cells stimulated with tetanus toxoid and harvested as described in E. S. Kleinerman et al., "Defective Monocyte Killing in Patients With Malignancies and Restoration of Function During Chemotherapy", *Lancet*, 2(8204), pp. 1102-05 (1980). The results shown are expressed as mean CPM±1 SE of tritiated thymidine uptake added on day 6 of cultures run in triplicate. We obtained similar results from 12 different measurements representing five separate batches of uromodulin from different donors. The mean CPM of 12 control cultures was 37,736±7,029; cultures with 3.5 $10^{-9}$M uromodulin exhibited 14,448±4,170. Inhibition ranged from 42% to 91% [t(11)=5.89, P=0.0002]. Using our assay, which measures the inhibition of antigen-specific T cell proliferation, we found that uromodulin exhibits a broad dose-response curve with activity demonstrable from $10^{-9}$ to $10^{-11}$M. See FIG. 4a. Additionally, uromodulin exhibited no apparent antigen specificity, as it inhibited the proliferation of the following antigens: tetanus toxoid, streptokinase-streptodornase and *Candida*. We found that addition of uromodulin only 12 hours later resulted in failure of inhibition. Furthermore, uromodulin had no effect on cell viability even after seven days of culture in vitro. Thus, uromodulin was immunosuppressive only if added at the initiation of a 6-day culture. See FIG. 4B.

We also added uromodulin to in vitro assays of B-cell and monocyte function. First, we assayed B-cell function with a sensitive reverse-hemolytic plaque assay which measures the total number of antibody-secreting cells after polyclonal stimulation with pokeweed mitogen. We enumerated the plaque-forming cells on day 7 according to H. Kirchner et al., "Polyclonal Immunoglobulin Secretion by Human B Lymphocytes Exposed to Epstein - Barr Virus In Vitro", *J. Immunol.*, 122, p. 1310-13 (1979), and concluded that uromodulin did not affect this assay of B-cell function.

We also used uromodulin in an assay which measures the in vitro development of spontaneous monocyte-mediated cytotoxicity in humans. This assay is regulated by suppressor cells and is sensitive to a number of exogenous agents capable of modulating monocyte function (E. S. Kleinerman et al., "Defective Monocyte Killing in Patients With Malignancies and Restoration of Function During Chemotherapy", *Lancet*, 2(8204), pp. 1102-05 (1980); E. S. Kleinerman, L. A. Zwelling, R. Schwartz and A. V. Muchmore, "Effect of L-Phenylalanine Mustard, Adriamycin, Actinomycin D, and 4'-(9-acridinyl-amino)methanesulfon-m-anisidide on Naturally Occurring Human Spontaneous Monocyte-Mediated Cytotoxicity", *Cancer Res.*, 42, pp. 1692-95 (1982)). We added purified uromodulin obtained by the process set forth above in varying concentrations at the initiation of culture. After 6 days, we resuspended the cells and counted them for viability using trypan blue exclusion (viability ranged from 85% to 95% with no difference noted between treated and untreated cultures). We added two hundred thousand viable cells to microtiter dishes and assayed cytotoxicity in triplicate using $^{51}$Cr labeled chicken red blood cell targets. Our results are expressed as mean % $^{51}$Cr release±1 SE of cultures run at a 1:1 target to effector cell ratio. See FIG. 4B. We found uromodulin to be a potent inhibitor of spontaneous monocyte toxicity when added at the beginning of culture, acting at concentrations as low as $10^{-11}$M.

These data suggest that the primary site of action of uromodulin is likely to be at the monocyte or T cell level and that uromodulin does not acting by nonspecifically blocking cellular division or by blocking IL-2 function, as these two mechanisms of action would also inhibit proliferation at later stages as well as the initiation of culture.

These results demonstrate that uromodulin blocks in vitro generation of spontaneous monocyte mediated cytotoxicity. Without being bound by theory, we believe that uromodulin blocks early events required for a normal in vitro antigen specific T cell proliferation response. Because uromodulin acts early in the sequence of events required for a T cell proliferation response and is ineffective later in culture, we believe that uromodulin does not block proliferating cells.

ELISA With Uromodulin Against IL-1 Coated Plates

IL-1 is a 15 kilo dalton macrophage-derived protein which effects a variety of immunostimulatory and inflammatory responses and which is believed to mediate the first step in such responses. IL-1 induces fever, causes the release of collagenase by synovial cells, induces prostaglandin synthesis by fibroblasts and acts as a co-mitagen. In addition, IL-1 has been also found to mediate acute phase reactant synthesis by hepatocytes and IL-2 synthesis by thymocytes. All of these activities suggest that IL-1 may play a central role in the regulation of diverse inflammatory host responses, and in the regulation of cellular differentiation and proliferation. We believe that uromodulin is the first isolated and characterized substrate for IL-1. As shown in the following assays, uromodulin specifically inhibits IL-1 by binding to it. This binding activity indicates that uromodulin is useful as an immunosuppressive or antiinflammatory agent.

Figure 5:
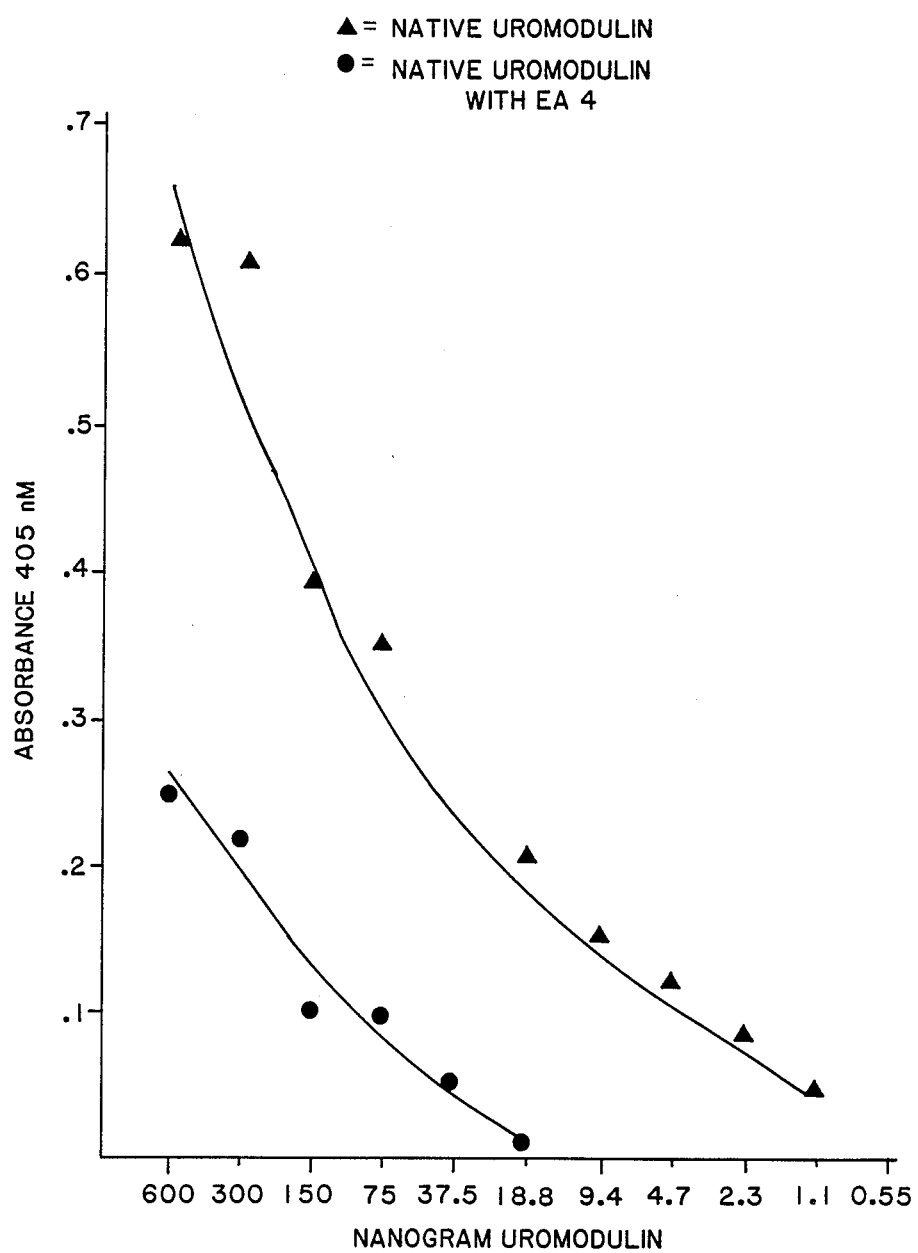
FIG. 5 displays in graphic form the specificity of uromodulin for interleukin-1.

Using the purified uromodulin obtained by the process set forth above and a SP-2 fusion partner, we produced a series of monoclonal antibodies raised against uromodulin using the method described in R. H. Kennett, *Monoclonal Antibodies*, pp. 365-80 (R. H. Kennett, T. J. McKearn & B. Bechtol ed. 1980). We then coated 96 well ELISA plates (Immulon, Dynatech, Virginia, U.S.A.) overnight with 1 $\mu$g/ml recombinant murine IL-1 having a specific activity of $5 \times 10^6$ U/mg of protein (generous gift of Dr. Peter Lomedico, Hoffman-LaRoche, Nutley, N.J., U.S.A.) in pH 9.6 carbonate buffer. This recombinant IL-1 may also be prepared according to the method described in P. Lomedico et al., "Cloning And Expression Of Murine IL-1 In *E. Coli*", *Nature*, 312, p. 418 (1984). We next washed these plates three times with phosphate-buffered saline with added Tween 20. We added uromodulin at various concentrations and allowed it to incubate for 2 hours at room temperature. We added 2 $\mu$l/ml of monoclonal anti-uromodulin EA4, a monoclonal antibody developed using uromodulin as an immunogen, to some wells to demonstrate competition. We then washed these plates with phosphate-buffered Tween 20 and allowed a 1:400 dilution of rabbit heteroantisera directed against uromodulin to incubate for an additional two hours. We then washed the plates 3 times. The presence of bound uromodulin was detected using an unmodified uromodulin specific antiserum and bound rabbit IgG was detected using an alkaline phosphatase modified goat anti-rabbit antiserum (Sigma, St. Louis, Mo., U.S.A.), as described in A. Voller, D. Bidwell and A. Bartlett", "Enzyme Linked Immunosorbent Assay", *Manual of Clinical Immunology*, p. 359 (N. R. Rose & H. Friedman ed. 1980). Changes in OD were measured at 405 nm using an appropriate alkaline phosphatase substrate. As shown in FIG. 5, uromodulin binds with high affinity to IL-1.

We next coated Immulon plates (Dynatech, Virginia) with 2 $\mu$g/ml of recombinant IL-1 in carbonate buffer (pH =9.6) for 18 hours. We then washed these plates three times in phosphate-buffered saline with 1% Tween 20 (PBS Tween). We then added various mixtures of uromodulin with or without competing substances such as carbohydrates, uromodulin derivatives or other unrelated glycoproteins, and incubated the plates for 2 hours at room temperature. We then washed the plates three times and added a 1:400 dilution of monospecific rabbit anti-uromodulin for one hour. We washed the plates another three times. We detected the presence of bound rabbit antisera by using a solid phase purified alkaline phosphatase modified good anti-rabbit immunoglobulin. We found that uromodulins specifically binds to IL-1 with a $K_d$ of $3 \times 10^{-10}$M.

We next coated 96 well Immunlon microtiter plates (Dynatech, Alexandria, Va., U.S.A.) with 2 $\mu$g/ml recombinant murine IL-1 in carbonate buffer (pH =9.6) and incubated them overnight (eighteen hours) at 4° C. We then washed the plates 3 times with PBS Tween.

Figure 6A:
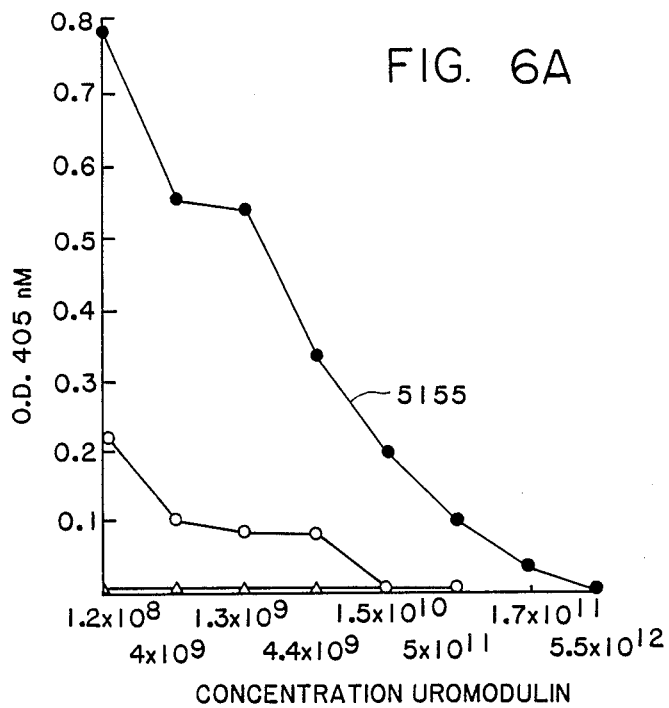
FIG. 6 depicts the binding activity of antisera specific for uromodulin to interleukin-1.

We added various concentrations of uromodulin, as prepared in above, to some of the wells and incubated the plates for 2 hours at room temperature. We then washed the plates with Tween-20 and added one of three antisera specific for uromodulin, i.e., 5155 (rabbit IgG, 1:800 dilution), CG7 (monoclonal IgM, 10 $\mu$g/ml) or EA4 (monoclonal IgG, 10 $\mu$g/ml) to the wells and incubated the plates for another 1 hour at room temperature. Subsequently, we washed the plates 3 times with Tween-20 and developed them with an alkaline phosphatase modified goat anti-rabbit or goat antimouse antiserum (Sigma, St. Louis, Mo., U.S.A.) using Sigma 104 substrate. We then analyzed the plates spectrophotometrically at 405 nm using a Dynatech (Virginia) microplate reader. The results are depicted in FIG. 6A, in which background absorbance (0.060 to 0.15 OD units) consisting of all reagents has been subtracted out. As shown in that figure, 5155 detected high affinity binding of uromodulin to IL-1 coated plates and could measure levels as low as $10^{-11}$M. CG7 was much less efficient than the rabbit heteroantisera but could also detect bound uromodulin. EA4 failed to detect bound uromodulin under all conditions, suggesting that EA4 and IL-1 might bind to identical or nearby epitopes. No significant binding was observed in the absence of IL-1.

Figure 6B:
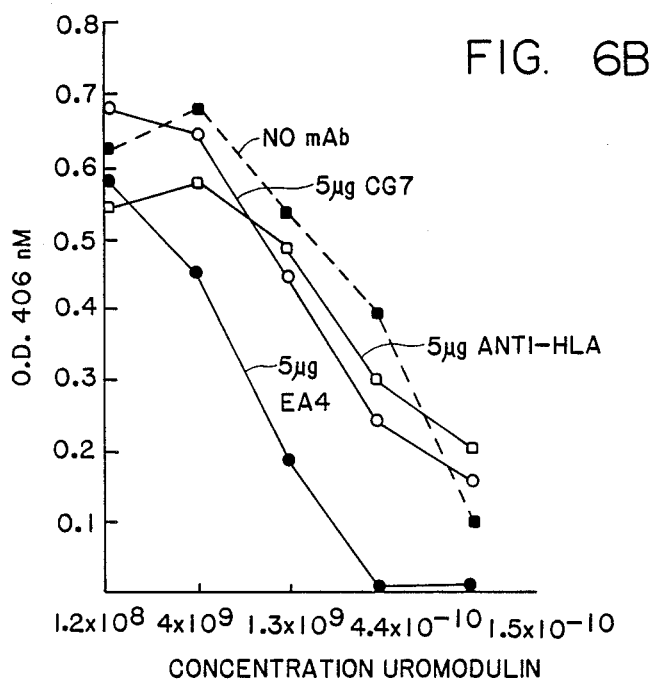

A similar assay to that described above was also run, with the exception that 5 $\mu$g of 5155, EA4 or anti-HLA (IgG1 monoclonal, Cappel, West Chester, Pa., U.S.A.) were added with uromodulin and allowed to incubate for 2 hours. The plates were washed and probed for bound uromodulin with 5155 and further developed for bound rabbit immunoglobulin as above. The results, depicted in FIG. 6B, show that EA4 but not CG7 or anti-HLA (an unrelated monoclonal IgG) competes with the binding of uromodulin to IL-1 coated plates. Further specificity controls run under similar conditions demonstrated that purified uromodulin failed to bind to uncoated ELISA plates or ELISA plates coated with other growth factors, such as IL-2, transferrin or insulin, or unrelated proteins, bovine serum albumin or fetal calf serum. Additionally, in analogous assays, recombinant murine IL-1 specifically bound to uromodulin-coated plates using IL-1 specific rabbit antiserum.

Inhibitory Effect of Uromodulin In An Assay Specific For IL-1 Induced Cell Proliferation The following demonstrates that uromodulin inhibits the activity of IL-1 in a standard mouse thymocyte comitagenic assay for IL-1 at concentration of $10^{-9}$ to $10^{-10}$ (3.7 ng = $4.3 \times 10^{-10}$M).

In this assay, we incubated $10^6$ C3H/HEJ thymocytes from mice less than 6 weeks old in 1PMI 1640 with 10% fetal bovine serum, with or without 1 μg of PHA (Burroughs Wellcome, North Carolina, U.S.A.). Various concentrations of uromodulin or human chorionic gonadotropin (run as a control) were added at the initiation of culture. We then added ultrapure human IL-1 (5U) (Genzyme, Boston, Massachusetts, U.S.A.) to all cultures except where noted. After 3 days, the cultures were pulsed with 0.5 microcuries of $^3$H thymidine for 6 hours and counted. The results, shown below, represent the mean of triplicate determinations:

| Nanograms added | Uromodulin (CPM) | HCG (CPM) |
| --- | --- | --- |
| 100 | 2021 | 12323 |
| 33 | 4234 | 15530 |
| 11 | 4201 | 14531 |
| 3.7 | 5694 | 14612 |
| CPM - no stimulant - 252 | | |
| CPM - PHA alone - 2467 | | |
| CPM - PHA + 5U IL-1 - 13461 | | |

As shown in this table, uromodulin inhibits the standard mouse thymocyte co-mitogenic assay for IL-1 activity.

ELISA With Uromodulin Against TNF-Coated Plates

Tumor necrosis factor (TNF) is produced by macrophages and mononuclear phagocytes and is selectively cytotoxic or cytostatic in vitro for a broad range of animal and human tumor cells (K. Haranaka and N. Satomi, "Note: Cytotoxic Activity of Tumor Necrosis Factor (TNF) on Human Cancer Cells in Vitro," *Japan J. Exp. Med.*, 51, pp. 191–94 (1981)). As shown in the following assays, uromodulin specifically binds to TNF at a site different from that at which uromodulin binds to IL-1. We believe that uromodulin is the first compound to be isolated and characterized to which both IL-1 and TNF bind. This binding activity indicates that uromodulin is useful as an immunosuppressant and antiinflammatory agent.

Figure 7A:
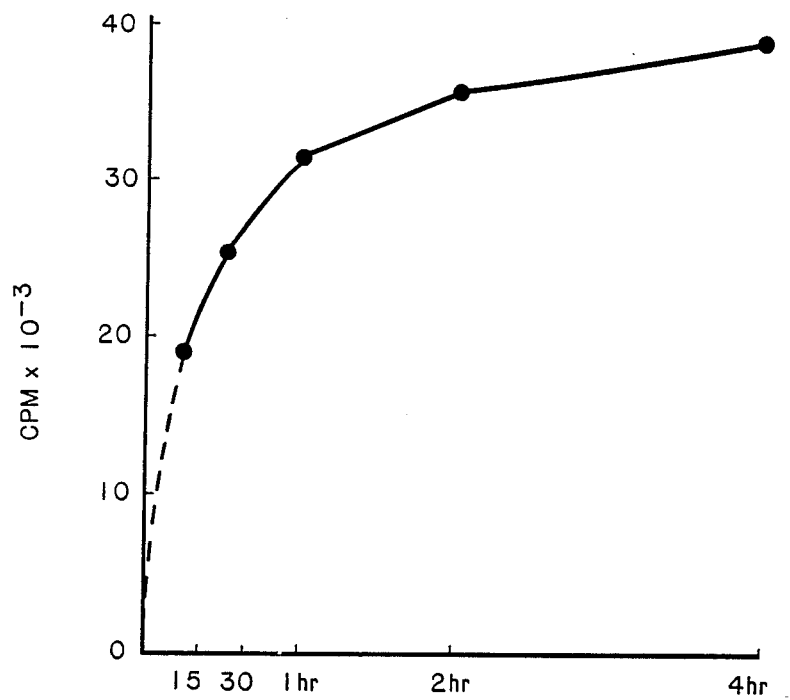
FIG. 7a depicts the kinetics of binding of uromodulin to TNF.
Figure 7B:
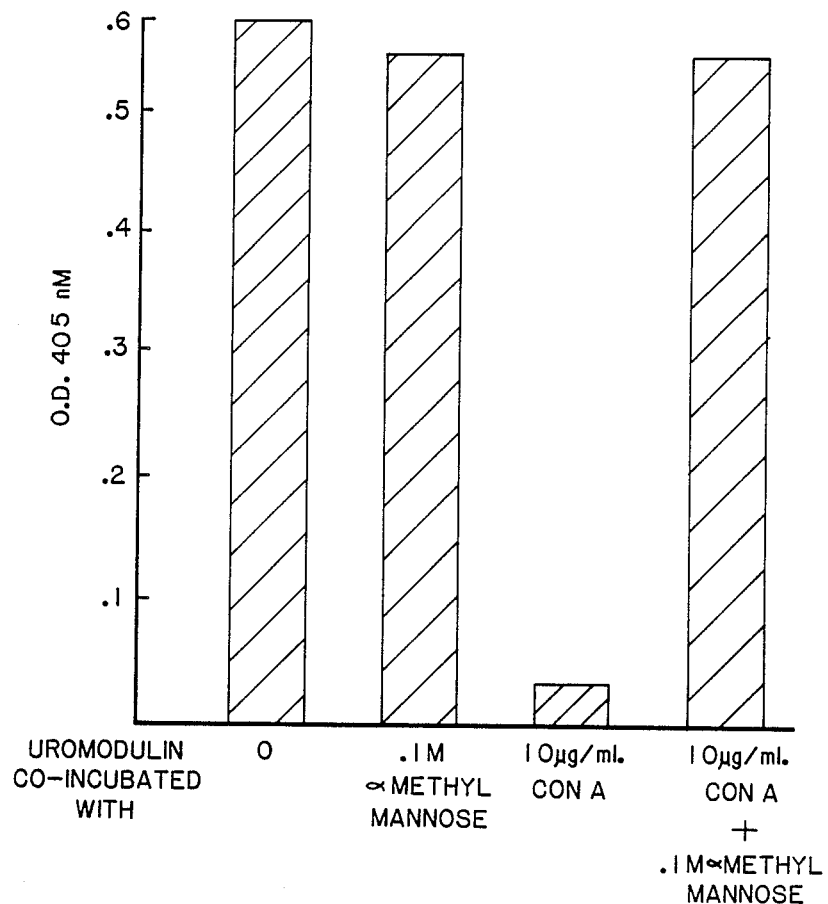
FIG. 7B depicts the inhibition by Con-A of IL-1 binding to uromodulin.
Figure 7C:
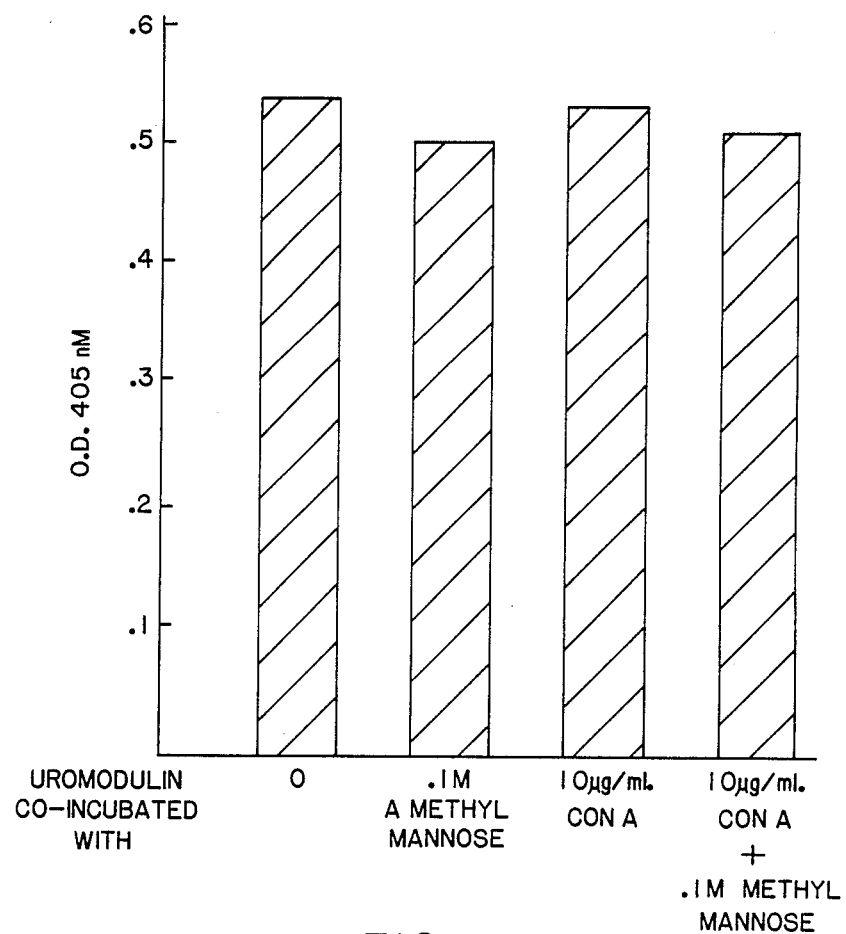
FIG. 7C depicts the failure of Con-A to compete with TNF for binding to uromodulin.
Figure 7D:
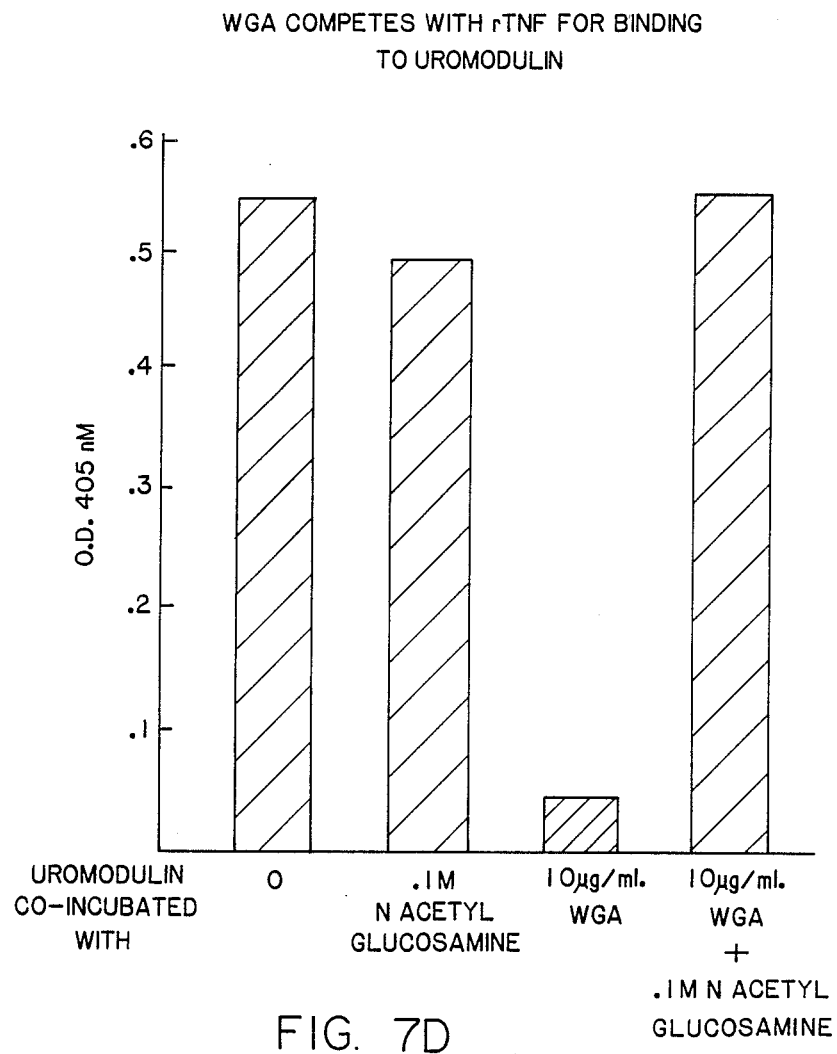
FIG. 7D depicts the inhibition by wheat germ agglutinin of TNF binding to uromodulin.

We followed the procedures set forth supra for the ELISA against IL-1 coated plates using recombinant TNF (Biogen, Cambridge, Mass., U.S.A.—specific activity 1 million U/mg) alone or in the presence of Con-A, or wheat germ agglutinin in place of the IL-1. The results, of these assays are depicted in FIG. 7. FIG. 7a depicts the kinetics of binding of uromodulin to TNF. Panel B depicts in graphic form the inhibition by Con-A, a lectin, of IL-1 binding depicts to uromodulin. FIG. 7C depicts in graphic form the failure of Con-A to compete with TNF for binding to uromodulin. FIG. 7D depicts in graphic form the inhibition by wheat germ agglutinin (WGA), another lectin, of TNF binding to uromodulin. WGA blocks the binding of TNF to uromodulin by covering the carbohydrate portion of the molecule. These data demonstrate that both IL-1 and TNF specifically bind to uromodulin and that IL-1 and TNF bind to uromodulin at different sites on the carbohydrate portion of the molecule.

C. The Role Of The Carbohydrate Portion Of Uromodulin In The Biological Activity Of Uromodulin The following examples demonstrate the important role that the carbohydrate portion of uromodulin plays in the activity of uromodulin.

In these examples, the purified uromodulin starting material was prepared from the urine of women in the second and third trimester of pregnancy as described supra, but it was not subjected to isoelectric focusing. Instead, approximately 12 liters of first void morning urine was passed over 600 cc of immobilized Con A Sepharose (Pharmacia, Uppsala, Sweden) in a large sintered glass funnel. We washed away any unbound material with four bed volumes of PBS and eluted the bound material with two bed volumes of 250 mM alpha methyl mannose in PBS. We then dialyzed the eluate against four changes of distilled water and lyophilized the material. Subsequently, we resuspended the material in PBS and separated it on a $1.2 \times 120$ cm Fractogel 55S column (Merck, Rahway, N.J., U.S.A.). We then collected, dialyzed and lyophilized the void volume.

Figure 8:
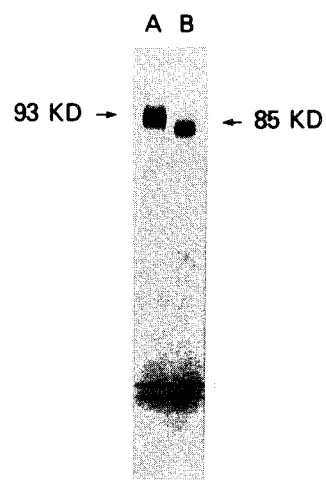
FIG. 8 depicts an SDS-PAGE analysis of reduced and unreduced uromodulin.

This procedure yielded uromodulin which was substantially homogeneous on 12.5% SDS-PAGE, carried out as described in U. K. Laemmli, "Cleavage of Structural Proteins During the Assembly of the Head of the Bacteriophage T4", *Nature*, 227, p. 680 (1970) in which gels were stained with a sensitive silver stain according to C. R. Merril, R. C. Switzer and A. Van Keuren, "Trace Polypeptides in Cellular Extracts and Human Body Fluids Detected by Two Dimensional Electrophoresis and a Highly Sensitive Silver Stain", *Proc. Natl. Acad. Sci. USA*, 76, pp. 4335 (1979). A 12.5% SDS-PAGE analysis of reduced and unreduced uromodulin is shown in FIG. 8. The apparent increase in molecular size of the reduced uromodulin (Lane A) suggests that uromodulin exists as a single polypeptide with intra-chain disulfide bonds.

Carbohydrate Content Of Uromodulin

In the following examples, we chemically modified our purified uromodulin to determine the role of its carbohydrate portion in the biological activity of the molecule.

First, we assessed the presence of sialic acid in the purified uromodulin prepared above by methods using purified neuraminidase and $H_2SO_4$ to hydrolyze that sugar from the intact glycoprotein. The total sialic acid released was measured using a sensitive method based on thiobarbituric acid, as described in K. S. Hammon and Papermaster "Flurometric Assay of Sialic Acid in the Picomole Range, A Modification of the Thiobarbituric Acid Assay", *Anal. Bio. Chem.*, 74, p. 292 (1976). Both methods revealed the presence of large quantities of sialic acid, with the $H_2SO_4$ method yielding estimates of 7-10% w:w sialic acid. We then measured the total amount of carbohydrate following acid hydrolysis and measurement of sugars using the anthrone method (R. G. Spiro, "Analysis of Sugars Found in Glycoproteins", *Methods in Enzymology*, Vol. III, pp. 1-5 (E. F. Neufeld & V. Ginsburg ed. 1966)). By this method, we determined that uromodulin is approximately 30% w/w sugar and rich in sialic acid. We then assessed the role of the carbohydrate portion of uromodulin in the biological activity of the molecule. To do this, we prepared various carbohydrate derivates of uromodulin.

We obtained a succinylated derivative of uromodulin by treating 1 ml of purified uromodulin (1 mg/ml) in 0.01M sodium bicarbonate buffer of pH 8.2 with a 50 molar excess of an acetone solution of succinic anhydride (100 mg/ml). As the addition of succinic anhydride caused the pH of the reaction mixture to drop, we added sodium hydroxide to maintain the pH of the solution at 8.2. We allowed the reaction mixture to stand at room temperature for two hours, then dialyzed the mixture for 18 hours against 0.01M ammonium bicarbonate buffer to obtain the succinylated derivative of uromodulin in which the native protein configuration had been altered (pH =7.5).

We next prepared a reduced and carboxymethylated derivative of uromodulin by dialyzing 1 ml of purified uromodulin (1 mg/ml) overnight against 100 volumes of 6M guanidine HCL containing 0.01M dithiothreitol. We then covered the reduced denatured glycoprotein with aluminum foil and added a 50 molar excess of sodium iodoacetate. We allowed this reaction to proceed in the dark for two hours. We separated the modified protein from the low molecular weight reactants by passing it over a column of Sephadex G-25 (Pharmacia, Uppsala, Sweden). This treatment resulted in a derivative of uromodulin in which internal sulfylhydryl bonds were broken, leading to unfolding of the native protein.

We then analyzed the succinylated and reduced and carboxymethylated uromodulin derivatives prepared above to confirm that their protein structure had been altered. First, we compared each derivative to unmodified uromodulin for the ability to bind the EA4 monoclonal antibody which is protein specific, and requires native configurations for binding.

Figure 9:
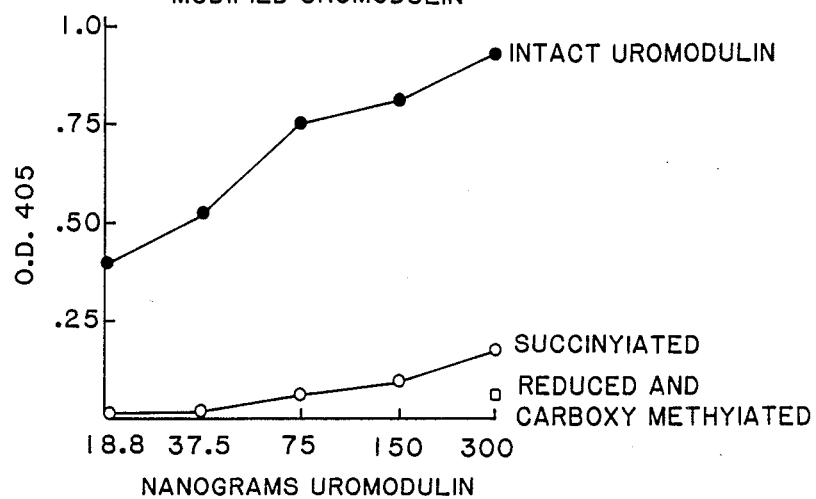
FIG. 9 depicts the ability of EA4, an anti-uromodulin antibody; to recognize intact vs. modified uromodulin.

To carry out this comparison, we used a variation of the ELISA assay described supra. We coated 5 $\mu$g/ml of EA4 in carbonate buffer (pH=9.6) onto ImmunIon microtiter plates and incubated the plates overnight at 4° C. We washed the plates with Tween-20 and then incubated them with either a modified uromodulin or intact uromodulin for another 2 hours at room temperature. We washed the plates with and then detected the presence of bound uromodulin using 1:400 dilution of our rabbit anti-uromodulin described supra. The presence of bound rabbit antiserum was detected using an alkaline phosphatase modified rabbit antiserum (Sigma, St. Louis, Mo., U.S.A.). The results are shown in FIG. 9, in which background OD in the presence of all reagents except uromodulin (0.090) was subtracted from all values. As demonstrated in that figure, succinylation and reduction and carboxymethylation essentially negated the ability of EA4 to recognize the modified forms of uromodulin demonstrating that EA4 specifically binds to the N-linked carbohydrate moiety.

Figure 10:
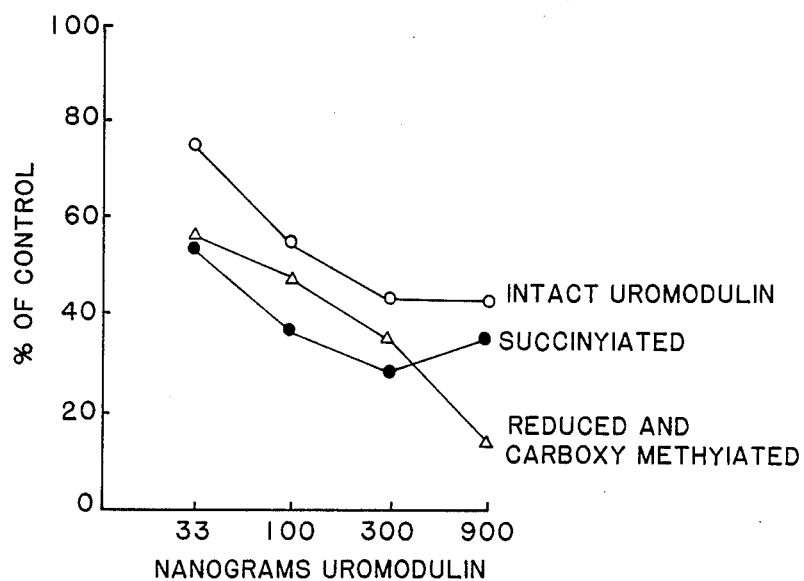
FIG. 10 depicts the biological activity of intact vs. modified uromodulin.

Next, we compared the biological activity of these modified uromodulin derivatives to that of unmodified uromodulin in our standard T cell proliferation assay. The results of the assay, shown in FIG. 10, represent triplicate determinations expressed as a percentage of control values with no uromodulin (12,540+2,100 CPM (ISE)) with background CPM in the absence of tetanus toxoid (140 CPM). As demonstrated in that figure, the uromodulin derivatives retained the in vitro biological activity of unmodified uromodulin.

We then predigested pronase-(10 mg/ml) in 0.01M Tris HCL buffer (pH =8.0) containing 0.01M calcium chloride at 37° C. for two hours to destroy any glycohydrolases present in the pronase preparation. Although we used pronase in this example, any proteolytic enzyme useful to digest proteins to yield carbohydrates may also be employed. Following this procedure, no intact protein of any size could be detected on 12.5% silver stained SDS-PAGE. We then added 25 $\mu$l of pre-digested pronase to 1 ml of purified uromodulin (1 mg/ml) in the same buffer and heated the mixture to 60° C. We incubated the mixture for six hours, then added a second 25 $\mu$l aliquot of pronase. We added a third 25 $\mu$l aliquot after 22 hours of incubation. We terminated the reaction after 30 hours by boiling it for 3 minutes. We removed the precipitate by centrifugation at 10,000XG. We placed the supernatant on a 0.7×50 cm Bio-Gel P-4 column (Bio-Rad, Richmond, Calif., U.S.A.) and eluted it with 0.01M ammonium bicarbonate buffer (pH =7.5). Eluted carbohydrate was detected using the anthrone method as described by Spiro supra. Protein was estimated by measuring absorbance at 280 nm.

Figure 11:
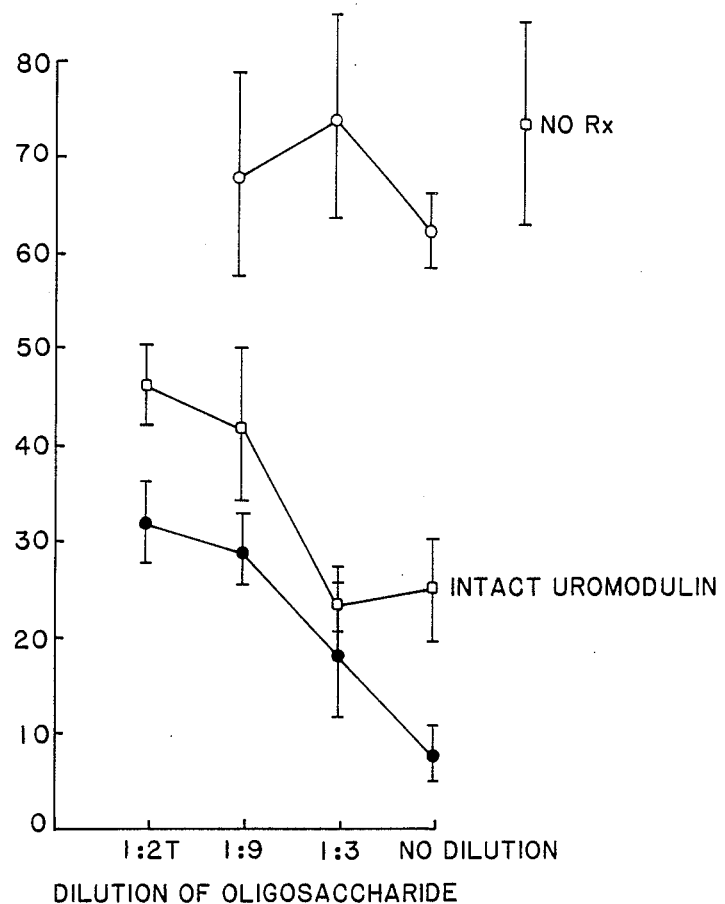
FIG. 11 depicts the biological activity of pronase digested uromodulin.

We pooled the first peak from this column, which contained the majority of the carbohydrate, and exhaustively lyophilized it to remove the volatile buffer. We also collected control peaks to run in parallel. These fractions were then resuspended in distilled water to their original starting volume and various dilutions were tested in our T cell proliferation assay for biological activity. The results of this assay are shown in FIG. 11, in which results are expressed as CPM ±1 SE of triplicate determinations and in which no added uromodulin gave 74,400 CPM±8500. As demonstrated in that figure, the carbohydrate peak contained all of the biological activity of these various fractions. Furthermore, the carbohydrate peak wa actually more active than intact uromodulin, based on its ability to induce greater inhibition of T cell proliferation.

Since pronase digestion yielded all available carbohydrate moieties of uromodulin, we attempted to selectively digest the molecule to release only the N-linked carbohydrate moieties based on the supposition that the N-linked carbohydrates constitute the biologically active portion of uromodulin. We digested 1 ml of purified uromodulin (1 mg/ml) in 0.2M sodium phosphate buffer (pH=8.8) containing 5 mM EDTA with 2.6 units of N-glycanase, an enzyme specific for N asparagine-linked oligosaccharides (Genzyme, Boston, Mass., U.S.A.). Although we used N-glycanase in this example, any endoglycosidase effective to digest proteins to yield N-linked carbohydrates may also be employed. We incubated the reaction mixture at 37° C. for 48 hours, then separated the reaction mixture on a 0.7×50 cm Bio-Gel P-4 column (Bio-Rad, Richmond, Calif., U.S.A.). We estimated protein by its emission intensity at 330 nm and carbohydrate content was estimated by the anthrone procedure supra. N-glycanase treatment decreased the apparent molecular weight of uromodulin on 12.5% SDS-PAGE by approximately 10 kD.

Figure 12:
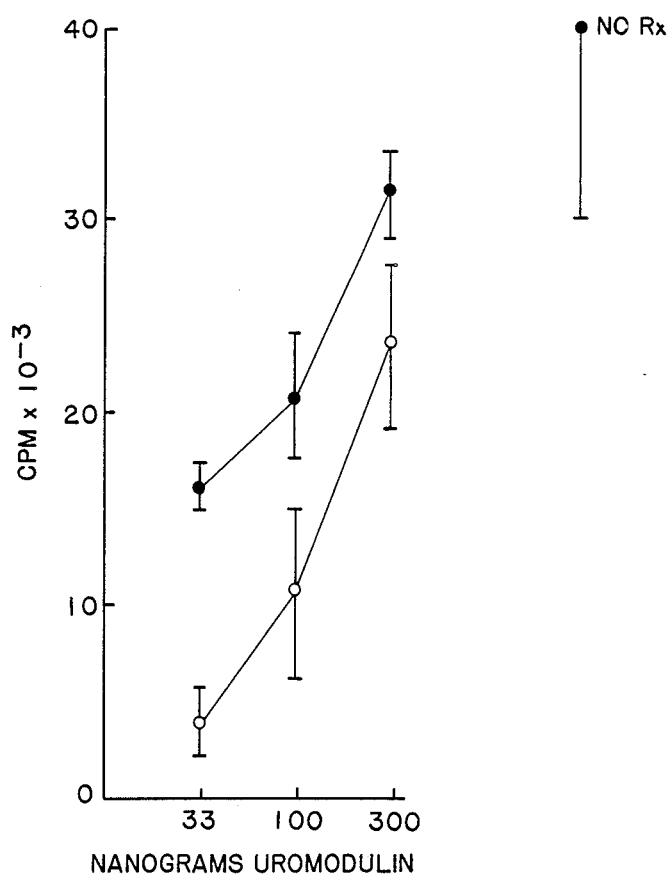
FIG. 12 depicts the biological activity of N-glycanase digested uromodulin.

We tested the N-glycanase digested uromodulin for in vitro bioactivity in our T cell proliferation assay. The results, shown in FIG. 12, are expressed as CPM+1 SE of triplicate determinations. As demonstrated in that figure, this modified uromodulin was at least as active as its undigested counterpart.

We then analyzed the ability of N-glycanase digested uromodulin to bind to IL-1 coated plates in a variation of our previously described ELISA assay. In this modified assay, we coated microplate wells with 1 $\mu$g/ml of recombinant IL-1 in carbonate buffer (pH=9.6). After washing the plates, we then added various concentrations of unmodified uromodulin or N-glycanase digested derivatives in PBS Tween to the washed IL-1 coated plates and incubated them for 2 hours at room temperature. We washed and developed the plates with our uromodulin specific rabbit heteroantiserum. The results are shown in FIG. 13, in which background absorbance in the absence of uromodulin (0.08) was subtracted from all values and results are expressed at 405 nm.

As demonstrated in FIG. 13, the N-glycanase digested uromodulin failed to bind efficiently to IL-1 coated plates, thus suggesting that the carbohydrate portion of uromodulin is responsible for the binding of uromodulin to IL-1.

This conclusion was further supported by the following ELISA assay. In this assay, we took 500 ng of uromodulin and digested it with N-glycanase. We then lyophilized the digested uromodulin to dryness and resuspended it in a 40:40:20 suspension of isobutanol, ethanol and water. After a 1 hour extraction period, we centrifuged the precipitate at 10,000XG, lyophilized the soluble material and resuspended it in water. Various quantities of this extract or a control preparation of ovalbumin were added along with 40 ng of uromodulin to IL1 coated microtiter plates incubated, washed and developed as described supra.

As shown in the table below, the isobutanol:ethanol:water extract of N-glycanase treated uromodulin totally blocked binding of unmodified uromodulin, further evidencing that IL-1 binds to uromodulin via N-linked sugars.

|  | OD 405 nM* |
| --- | --- |
| 40 ng uromodulin | 485 |
| 40 ng uromodulin +5 µl extract | 86 |
| 40 ng uromodulin +2.5 µl extract | 181 |
| 40 ng uromodulin +1.2 µl extract | 121 |
| 40 ng uromodulin +0.6 µl extract | 244 |
| 40 ng uromodulin +5 µg ovalbumin | 513 |
| 40 ng uromodulin +5 µg N-glycanase | 490 |
| digest of ovalbumin | |

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

I claim:

1. Substantially pure Uromodulin protein having the following characteristics: (a) a molecular weight of 85 kilodaltons, as determined by SDS-PAGE, (b) a carbohydrate content of approximately 30% w/w, (c) specifically binds to lectins, (d) specifically binds to interleukin-1 and (e) specifically binds to tumor necrosis factor.

2. A pharmaceutical composition comprising the Uromodulin protein of claim 1 and a pharmaceutically acceptable carrier.

3. A process for purifying uromodulin from crude urine comprising the steps of:
   (a) contacting the urine with an affinity column containing a lectin which recognizes mannose;
   (b) eluting uromodulin from the column; and
   (c) dialyzing small molecular weight contaminants from the uromodulin.

4. A process for purifying uromodulin from crude human urine comprising the steps of:
   (a) contacting the urine with an affinity column containing a lectin which recognizes mannose;
   (b) washing the column to remove components of the urine not bound to the column;
   (c) eluting uromodulin from the column;
   (d) dialyzing the small molecular weight contaminants from the uromodulin;
   (e) concentrating the uromodulin; and
   (f) eluting uromodulin by molecular sizing.

5. The process according to claim 4 wherein the crude urine comprises crude human pregnancy urine.

6. The process according to claim 3 further comprising the step of subjecting the uromodulin to isoelectric focusing.

* * * * *